United States Patent
Yonesaka et al.

(10) Patent No.: US 11,371,995 B2
(45) Date of Patent: Jun. 28, 2022

(54) METHOD FOR SELECTING INDIVIDUALS TO BE ADMINISTERED IMMUNE CHECKPOINT INHIBITOR

(71) Applicants: KINKI UNIVERSITY, Higashiosaka (JP); DAIICHI SANKYO COMPANY, LIMITED, Tokyo (JP)

(72) Inventors: Kimio Yonesaka, Osaka-Sayama (JP); Kazuhiko Nakagawa, Osaka-Sayama (JP); Kenji Hirotani, Tokyo (JP)

(73) Assignees: Daiichi Sankyo Company, Limited, Tokyo (JP); Kinki University, Osaka (JP)

( * ) Notice: Subject to any disclaimer, the term of this patent is extended or adjusted under 35 U.S.C. 154(b) by 248 days.

(21) Appl. No.: 16/473,615

(22) PCT Filed: Dec. 25, 2017

(86) PCT No.: PCT/JP2017/046503
§ 371 (c)(1),
(2) Date: Jun. 25, 2019

(87) PCT Pub. No.: WO2018/123999
PCT Pub. Date: Jul. 5, 2018

(65) Prior Publication Data
US 2020/0173999 A1 Jun. 4, 2020

(30) Foreign Application Priority Data

Dec. 28, 2016 (JP) .............................. JP2016-256899
Oct. 4, 2017 (JP) .............................. JP2017-194704

(51) Int. Cl.
*G01N 33/574* (2006.01)
*C07K 16/28* (2006.01)
*A61K 39/00* (2006.01)
*G01N 1/30* (2006.01)

(52) U.S. Cl.
CPC ... *G01N 33/57484* (2013.01); *C07K 16/2827* (2013.01); *G01N 1/30* (2013.01)

(58) Field of Classification Search
CPC combination set(s) only.
See application file for complete search history.

(56) References Cited

U.S. PATENT DOCUMENTS

| | | | |
|---|---|---|---|
| 5,811,097 A | 9/1998 | Allison et al. | |
| 2015/0118245 A1* | 4/2015 | Weber | C07K 16/3053 424/142.1 |
| 2019/0330350 A1* | 10/2019 | Freeman | C07K 16/3038 |

FOREIGN PATENT DOCUMENTS

| | | |
|---|---|---|
| JP | 4249013 B2 | 1/2009 |
| JP | 5885764 B2 | 2/2016 |

OTHER PUBLICATIONS

Sun et al (Lung Cancer, 2006, 53:143-151).*
Boland et al (Clinical Lung Cancer, 2013, 14:157-163).*
Ye et al (Cellular Physiology and Biochemistry, Sep. 2016, 39:1568-1580).*
Herbst et al (Nature, 2014, 515:563-567 and extended data).*
Garon et al (NEJM, May 2015, 372:2018-2028).*
Marin Acevedo et al (Journal of Hematology & Oncology, 2021, 14:45, internet pp. 1-29).*
Cai et al (Cellular & Molecular Immunology, 2020, 17:227-236).*
Aggarwal et al (Society for Immunotherapy of Cancer, 2018, ClinicalTrials.gov #NCT02475213; abstract #O24).*
Extended European Search Report dated Jul. 9, 2020, issued in corresponding Application No. EP 17885949.2, filed Dec. 25, 2017, 10 pages.
Mahoney, MD, PhD, K. M., et al., "The Next Immune-Checkpoint Inhibitors: PD-1/PD-L1 Blockade in Melanoma," Clinical Therapeutics 37(4): 764-782, Feb. 2015.
Gainor, J. F., et al., "EGFR Mutations and ALK Rearrangements Are Associated with Low Response Rates to PD-1 Pathway Blockade in Non-Small Cell Lung Cancer: A Retrospective Analysis," American Association for Cancer Research: Clinical Cancer Research 22(18): 4585-4593, May 2016.
Shukuya, MD, PhD, Takehito, and David P. Carbone, MD, PhD, "Predictive Markers for the Efficacy of Anti-PD-1/RD-L1 Antibodies in Lung Cancer," Journal of Thoracic Oncology: State of the Art: Concise Review 11(7): 976-988, Feb. 2016.
Shien, K., et al., "Predictive biomarkers of response to PD-1/PD-L1 immune checkpoint inhibitors in non-small cell lung cancer," Elsevier: Lung Cancer 99: 79-87, Jun. 2016.
Jiang, B., et al., "B7-H3 increases thymidylate synthase expression via the PI3k-Akt pathway," Tumor Biology 37(7): 9465-9472, Jan. 2016.
Miao, Y., et al., "B7-H1 and B7-H3 are independent predictors of poor prognosis in patients with non-small cell lung cancer," Oncotarget 6(5): 3452-3461, Dec. 2014.
Abdel-Rahman, O., "Correlation Between PD-L1 Expression and Outcome of NSCLC Patients Treated With Anti-PD-1/PD-L1 Agents: A Meta-Analysis," Critical Reviews in Oncology/Hematology 101:75-85, May 2016.
International Search Report and Written Opinion dated Apr. 17, 2018, issued in corresponding International Application No. PCT/JP2017/046503, filed Dec. 25, 2017, 9 pages.

* cited by examiner

*Primary Examiner* — Laura B Goddard
(74) *Attorney, Agent, or Firm* — Christensen O'Connor Johnson Kindness PLLC

(57) ABSTRACT

A method for selecting an individual to be a candidate for administration of an immune checkpoint inhibitor in treatment of a tumor, comprising: (1) a step of collecting a tumor tissue from the individual, (2) a step of determining the extent of B7-H3 expression in the tumor tissue collected in step (1), and (3) a step of selecting the individual as an individual to be a candidate for administration of the immune checkpoint inhibitor if the B7-H3 expression level is considered to be negative, is provided.

9 Claims, 3 Drawing Sheets

[Figure 1]
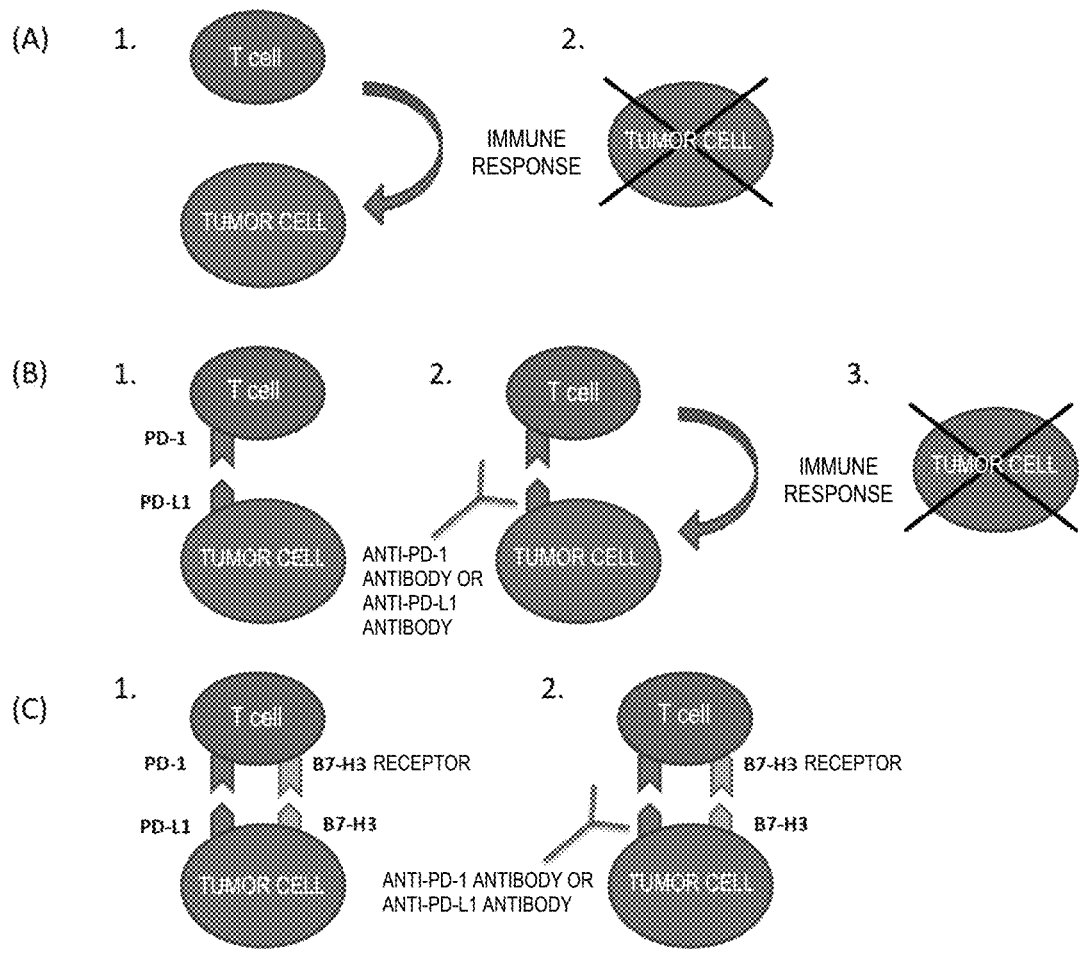

[Figure 2]
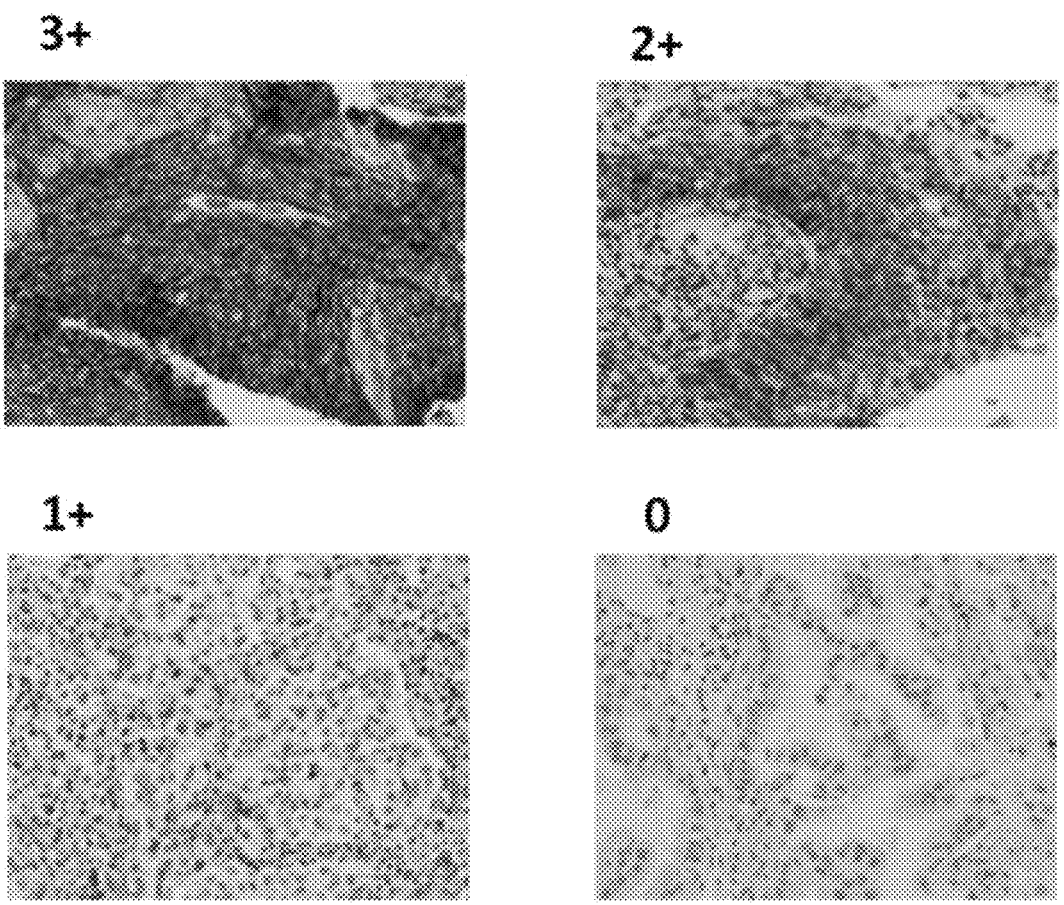

[Figure 3]
(A) CASES OF RESPONSE TO ANTI-PD-1 ANTIBODY
| B7-H3 IHC SCORE | % | n=19 |
|---|---|---|
| 3+ | 15.78947 | 3 |
| 2+ | 26.31579 | 5 |
| 1+ | 21.05263 | 4 |
| 0 | 36.84211 | 7 |
(B) CASES OF NON-RESPONSE TO ANTI-PD-1 ANTIBODY
| B7-H3 IHC SCORE | % | n=31 |
|---|---|---|
| 3+ | 25.80645 | 8 |
| 2+ | 48.3871 | 15 |
| 1+ | 22.58065 | 7 |
| 0 | 3.22580 | 1 |
(C)
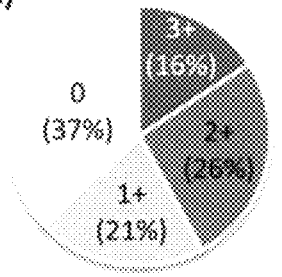
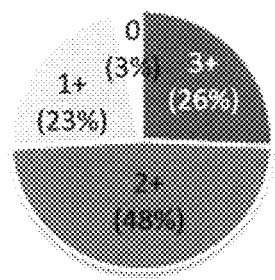
| | CASES OF RESPONSE | CASES OF NON-RESPONSE | RESPONSE RATE |
|---|---|---|---|
| B7-H3 positive | 12 | 30 | 29% |
| B7-H3 negative | 7 | 1 | 88% |
FISHER'S EXACT TEST, $p = 0.0031$

METHOD FOR SELECTING INDIVIDUALS TO BE ADMINISTERED IMMUNE CHECKPOINT INHIBITOR

TECHNICAL FIELD

The present invention relates to a method for selecting individuals to be a candidate for administration of an immune checkpoint inhibitor and more particularly to a method for selecting individuals for whom administration of an immune checkpoint inhibitor will be effective by collecting tumor tissue from individuals suffering from malignant tumors and determining the extent of B7-H3 expression in the collected tumor tissue.

BACKGROUND ART

Cancer is estimated to develop in one in two persons and kill one in three persons at present. Methods for treating cancer progress day by day and the cure rate and the survival rate are improving.

However, the death rate from cancer is still rising and the development of a new method of a treatment is desired.

In recent years, cancer immunotherapies have come into the limelight as new therapies for malignant tumors.

Several thousand tumor cells are considered to occur each day in the human body, but not all of them directly lead to the development of tumors. In the human body, the immune system's removal of tumors and the mechanism by which tumors survive always compete with each other and tumors develop when the latter outbalances the former.

Tumor cells have a mechanism for lowering the T cell immune function which functions by the interaction between membrane proteins present on the surface of lymphocytes such as T cells and proteins present on the surface of the tumor cells in order to survive (see 1 in FIG. 1B).

Meanwhile, cancer immunotherapies treat tumors by modifying the immune system present in patients to enhance the immunity for removing the tumors.

Immune checkpoint inhibitors, which inhibit the aforementioned mechanism that allows tumor cells to survive, such as anti-CTLA-4 antibodies (see Patent Literature 1), an anti-PD-1 antibody (Nivolumab, trade name Opdivo (R), see Patent Literature 2), and anti-PD-L1 antibodies (see Patent Literature 3), which are representative agents used in cancer immunotherapies, exhibit therapeutic performance exceeding conventional anticancer agents, and have been being approved for use in the treatment of many malignant tumors such as nonsmall-cell lung carcinoma, malignant melanoma, and kidney cancer.

However, not all malignant tumor cases are effectively treated with the aforementioned immune checkpoint inhibitors. Actually, there is data indicating that the response rate for nonsmall-cell lung carcinoma cases when an immune checkpoint inhibitor is used is about 20%.

Accordingly, when use of an expensive immune checkpoint inhibitor is expected to be ineffective, it is beneficial to avoid the ineffective use.

Therefore, there is a need for a method for determining whether or not the aforementioned agents for cancer immunotherapies are effective for those to be treated by administration thereof before starting therapy.

For example, it has been revealed that PD-1 is a membrane protein present on the surface of T cells and suppresses the activation of T cells by interacting with the ligand PD-L1. PD-L1 is constitutively expressed in tumor cells and the binding of PD-L1 on tumor cells with PD-1 on T cells suppresses the immune response which functions by the activation of T cells and, as a result, lowers the function of removing tumor cells by the activation of T cells.

A method of predicting the antitumor effect of anti-PD-1 antibody therapeutic agents in malignant tumor cases based on the expression level of the PD-L1 protein in tumor tissues by making use of the aforementioned relationship is known (see Non Patent Literature 1).

However, there is a problem that accurate prediction of the antitumor effect is not possible in all cases only by confirming the expression level of the PD-L1 protein.

CITATION LIST

Patent Literature

Patent Literature 1: U.S. Pat. No. 5,811,097
Patent Literature 2: Japanese Patent No. 4249013
Patent Literature 3: Japanese Patent No. 5885764

Non Patent Literature

Non Patent Literature 1: Correlation between PD-L1 expression and outcome of NSCLC patients treated with anti-PD-1/PD-L1 agents: A meta-analysis, Critical Reviews in Oncology/Hematology 101 (2016) 75-85.

SUMMARY OF INVENTION

Technical Problem

An object of the present invention is to provide a method for selecting individuals for whom administration of an immune checkpoint inhibitor will be effective and a method for treating a tumor, comprising treating the individual selected by the aforementioned method by administering the immune checkpoint inhibitor.

Solution to Problem

The present inventors have studied diligently to achieve the aforementioned object and found that it is possible to select individuals for whom administration of an immune checkpoint inhibitor will be effective by determining the extent of B7-H3 expression in tumor tissue collected from the individuals, thereby completing the present invention. Accordingly, the present invention encompasses the following inventions.

(1) A method for selecting an individual to be a candidate for administration of an immune checkpoint inhibitor in treatment of a tumor, comprising: (1) a step of collecting a tumor tissue from the individual, (2) a step of determining the extent of B7-H3 expression in the tumor tissue collected in step (1), and (3) a step of selecting the individual as an individual to be a candidate for administration of the immune checkpoint inhibitor if the B7-H3 expression level is considered to be negative.

(2) The method for selection according to the above (1), wherein step (2) comprises a step of conducting immunohistological staining of B7-H3.

(3) The method for selection according to the above (1) or (2), wherein the immune checkpoint inhibitor is an anti-PD-1 antibody, an anti-PD-L1 antibody, and/or an anti-CTLA-4 antibody.

(4) The method for selection according to the above (1), wherein the tumor is nonsmall-cell lung carcinoma, small cell lung carcinoma, neuroendocrine tumor, squamous cell carcinoma, adenocarcinoma, sarcoma, leukemia, neuroma, melanoma, lymphoma, or a cancer of unknown primary.

(5) The method for selection according to the above (4), wherein the nonsmall-cell lung carcinoma is adenocarcinoma, squamous cell carcinoma, or large cell carcinoma.

(6) The method for selection according to the above (4), wherein the adenocarcinoma is prostate carcinoma, small intestine carcinoma, endometrial carcinoma, cervical canal carcinoma, colorectal carcinoma, lung carcinoma, pancreatic cancer, esophageal carcinoma, rectal carcinoma, uterine carcinoma, gastric carcinoma, breast carcinoma, ovarian carcinoma, kidney cancer, hepatocarcinoma, gallbladder carcinoma, or bile duct carcinoma.

(7) The method for selection according to the above (4), wherein the squamous cell carcinoma is cervical canal carcinoma, eyelid carcinoma, conjunctival carcinoma, vaginal cancer, lung carcinoma, oral carcinoma, skin carcinoma, bladder carcinoma, tongue cancer, pharyngeal cancer, laryngeal carcinoma, or esophageal carcinoma.

(8) The method for selection according to the above (4), wherein the sarcoma is myogenic sarcoma.

(9) An immune checkpoint inhibitor for treating a tumor in an individual selected by a method according to the above (1).

(10) The immune checkpoint inhibitor according to the above (9), wherein the immune checkpoint inhibitor is an immune checkpoint inhibitor comprising an anti-PD-1 antibody, an anti-PD-L1 antibody, and/or an anti-CTLA-4 antibody.

(11) A method for treating a tumor, comprising treating an individual selected by a method according to any one of the above (1) to (10) by administering an immune checkpoint inhibitor.

(12) The method for treatment according to the above (11), wherein the immune checkpoint inhibitor is an immune checkpoint inhibitor comprising an anti-PD-1 antibody, an anti-PD-L1 antibody, and/or an anti-CTLA-4 antibody.

Advantageous Effects of Invention

According to the present invention, a method for more accurately and efficiently selecting individuals for whom an immune checkpoint inhibitor will be effective by collecting tumor tissue from individuals, determining the B7-H3 expression level in portions of the tumor tissue, and treating individuals for whom the B7-H3 expression level is considered to be negative by administration of the immune checkpoint inhibitor, and a method for treating tumors, comprising treating the individuals selected by the aforementioned method by administering the immune checkpoint inhibitor can be provided. Since the present invention makes it possible to determine the probability that an immune checkpoint inhibitor is effective before treatment, it is possible to avoid ineffective treatment that requires a large amount of medical expense, but is not expected to be effective, despite the existence of cases in which the immune checkpoint inhibitor is hardly likely to be effective.

BRIEF DESCRIPTION OF DRAWINGS

FIG. 1(A) is a schematic view illustrating the immune response of CD8-positive lymphocytes (T cells) to tumor cells; (B) FIG. 1(B) illustrates that the binding between PD-1 and PD-L1 suppresses the immune response, but the binding of an anti-PD-1 antibody or an anti-PD-L1 antibody to PD-1 or PD-L1 removes the suppression of the immune response and tumor cells are eliminated; and (C) FIG. 1(C) illustrates that the binding between B7-H3 and the B7-H3 receptor prevents the removal of the suppression of the immune response which functions by the binding between an anti-PD-1 antibody or an anti-PD-L1 antibody and PD-1 or PD-L1.

FIG. 2 illustrates examples of tumor tissues for which the B7-H3 immunohistochemistry (hereinafter, referred to as IHC) score was rated as 3+, 2+, 1+, 0 (all with a 20× objective lens) in B7-H3 immunohistological staining (IHC), based on the HER2 IHC evaluation criteria in breast cancer (Guidelines for HER2 testing in breast cancer, the fourth edition) by Breast Cancer HER2 Testing Pathology Group.

FIG. 3(A) illustrates the B7-H3 expression level in cases of response to an anti-PD-1 antibody in nonsmall-cell lung carcinoma; (B) FIG. 3(B) illustrates the B7-H3 expression level in cases of non-response to an anti-PD-1 antibody in nonsmall-cell lung carcinoma; and (C) FIG. 3(C) illustrates the number of cases in which the B7-H3 expression level is considered to be positive (B7-H3 (+), the cases in which the B7-H3IHC score was 3+, 2+, or 1+), the number of cases in which the B7-H3 expression level is considered to be negative (B7-H3 (−), the cases in which the B7-H3IHC score was 0), and the response rate in (A) and (B).

DESCRIPTION OF EMBODIMENTS

<PD-1 and B7-H3>

Even when tumor cells occur, they are usually eliminated by the immune response which functions by CD8-positive lymphocytes (T cells) (see, FIG. 1A).

PD-1, illustrated in FIG. 1B, is a membrane protein that belongs in the immunoglobulin superfamily and is expressed on the surface of CD8-positive T cells. Meanwhile, PD-L1, which is a ligand of PD-1, is a protein that is strongly expressed also on the surface of tumor cells.

The binding of PD-L1 with PD-1 on the surface of activated T cells results in the suppression of the T cell activity and the attenuation of the effect of eliminating tumor cells by T cells. Such a mechanism mediated by PD-1/PD-L1 represents the resistance of tumor cells against tumor immunity (see 1 in FIG. 1B).

Anti-PD-1 antibody preparations (Nivolumab and the like) and anti-PD-L1 antibody preparations have been developed for inhibiting such binding between PD-1 and PD-L1 and maintaining the immune response to tumors, which is inherently present in the living body (see 2 in FIG. 1B).

Meanwhile, B7-H3 is considered to be a protein expressed on the surface of tumor cells (see, e.g., The Journal of Immunology, 2004, vol. 172, p. 2352-2359) and to have the function of attenuating the T cell function of eliminating tumor cells by interacting with the B7-H3 receptor on T cells, like PD-L1 (see FIG. 1C).

According to the experimental findings by the present inventors, it is considered that the administration of an anti-PD-1 antibody preparation or an anti-PD-L1 antibody preparation as an immune checkpoint inhibitor to tumor tissue, of which the expression level of B7-H3 has been considered to be positive, in order to inhibit the binding between PD-1 and PD-L1 is hardly likely to produce the effect of administration of the anti-PD-1 antibody preparation or anti-PD-L1 antibody preparation, as long as the T cell function of eliminating tumor cells is attenuated by the binding of B7-H3 with the B7-H3 receptor (see 2 in FIG. 1C).

Accordingly, since the T cell function of eliminating tumor cells would be more likely to be induced if it is possible to inhibit the binding between PD-1 and PD-L1 and to inhibit the binding between B7-H3 and the B7-H3 receptor, methods for treating a tumor, of which the expression level of B7-H3 is considered to be positive based on the evaluation criteria described later, comprising administering an immune checkpoint inhibitor and a B7-H3 inhibitor (anti-B7-H3 antibody or the like) that binds to B7-H3 or a B7-H3 receptor inhibitor (anti-B7-H3 receptor antibody or the like) that binds to the B7-H3 receptor simultaneously or sequentially, or immune checkpoint inhibitors and/or B7-H3 inhibitors or B7-H3 receptor inhibitors for treating such tumors are included in the invention of this application and it is possible to treat such tumors more accurately and efficiently by using such a method of treatment or such inhibitors.

<Immune Checkpoint Inhibitor>

Examples of the immune checkpoint inhibitor, of which the antitumor effect against a tumor tissue can be predicted by measuring the expression level of B7-H3 in the tumor tissue, include anti-PD-1 antibody preparations, anti-PD-L1 antibody preparations, anti-CTLA-4 antibodies, and the like.

<Method for Measuring B7-H3 Expression Level>

The biological specimen to be used in the method for selection according to the present invention may be a specimen that is derived from a tissue or blood from a patient and that contains the tumor tissue.

The biological specimen is a specimen taken from the patient and may be a specimen acquired for the method for selection according to the present invention, but may also be a specimen acquired to be used for another test or a specimen taken by a surgical operation.

When a specimen is used, for example, in a test by immunohistological staining, a paraffin section prepared from a specimen obtained from the patient as a sample to be used in the test may be used. Moreover, when a specimen is used, for example, in quantitative PCR, an mRNA extract, which is prepared from a specimen obtained from the patient as a sample to be used in the examination, may be used.

A preferred method for determining the expression level of B7-H3 in the tumor tissue is a method involving an immunological technique, which is simple to perform.

For example, the expression level can be determined by immunostaining (including fluorescent antibody techniques, enzyme antibody techniques, heavy metal-labeled antibody techniques, and radiolabeled antibody techniques); a combination of separation by electrophoresis and detection or quantification by fluorescence, an enzyme, a radioisotope, or the like (including Western blotting and fluorescence two-dimensional electrophoresis); enzyme-linked immunosorbent assay (ELISA), dot blotting, or the like.

When immunostaining is used, the antibody to be used in the immunostaining may be any antibody as long as it is an antibody that specifically interacts with B7-H3 and is suitable for the staining of cells expressing B7-H3 in a histo-cytological preparation. Examples of such an antibody include an anti-human B7-H3 antibody (a product made by R & D SYSTEMS), an anti-CD276 antibody (a product made by Abcam plc., synonymous with an anti-B7-H3 antibody), and the like.

Moreover, the detection or quantification at the mRNA level can be conducted, for example, by RT-PCR (preferably real-time RT-PCR), Northern blotting, Branched DNA assay or the like.

Furthermore, when the expression level of B7-H3 in tumor cells in a blood sample is measured, it can be measured with a flow cytometer.

When mRNA is measured, total RNA from the tumor tissue collected is extracted. The extraction of total RNA can be conducted, for example, by guanidine thiocyanate/cesium chloride ultracentrifugation, guanidine thiocyanate/hot phenol extraction, guanidinium chloride extraction, or the like.

The transcription product of the gene may be measured by measuring the extent of gene expression using a nucleotide comprising all or a part of the nucleotide sequence of the gene encoding B7-H3 as a probe or a primer. The extent of gene expression can be measured by a method using a microarray (microchip), Northern blotting, quantitative PCR targeting the gene to be quantified or a fragment thereof, or the like.

If the B7-H3 expression level is considered to be negative, then it can be determined that the patient may be treated by the administration of an immune checkpoint inhibitor.

The signal intensity from a label may be determined by viewing under a microscope or by any method known in the art for detecting a label. For example, when a fluorescent material is used as a label, the fluorescence thereof may be detected by using a fluorescence microscope, a fluorescence plate reader, a fluorescence scanner, or the like. Moreover, when a radioisotope is used as a label, the radioactivity may be measured with a liquid scintillation counter, a γ-counter, or the like.

<Classification of B7-H3 Immunohistological Staining Results>

The classification of B7-H3 expression levels is preferably conducted by a pathologist, a clinician, a laboratory technician, or a laboratory having sufficient experience depending on the method for detection or quantification. For example, the classification of B7-H3 expression levels may be conducted by a pathologist when the immunohistological staining is used and conducted by a laboratory technician when RT-PCR is used.

When B7-H3 expression levels are classified into a plurality of grades by immunohistological staining, the immunohistological staining results may be classified, for example, as follows.

Only the staining and the staining intensity in the cell membrane of tumor cells are to be considered and the reaction in the cytoplasm is to be excluded from the consideration. As regards the staining in the cell membrane, if the staining intensity is high, then it is classified as "positive" (not to be treated by the administration of an immune checkpoint inhibitor) and if the staining intensity is low, then it is classified as "negative" (to be a candidate for the administration of an immune checkpoint inhibitor).

The terms "positive" and "negative" as applied to the staining intensity in the Description of this application are classified according to the evaluation criteria for tissue immunological staining set forth in Table 1.

Specifically, when [1] tumor cells with strong and complete circular cell membrane staining exceed 10% (IHC score 3+), [2] tumor cells with incomplete and/or weak to moderate and complete circular cell membrane staining exceed 10% or tumor cells with strong and complete circular cell membrane are present and 10% or less (IHC score 2+), or [3] tumor cells with partial cell membrane staining exceed 10% (IHC score+1), it is classified as "positive". Moreover, when [4] no staining is observed or tumor cells with incomplete and slight or faint cell membrane staining 10% or less (IHC score 0), it is classified as "negative".

<Disease to be Treated>

Examples of the tumors that can be treated by the invention of this application include nonsmall-cell lung carcinoma, small cell lung carcinoma, neuroendocrine tumor, squamous cell carcinoma, adenocarcinoma, and the like. Specific examples of the nonsmall-cell lung carcinoma include adenocarcinoma, squamous cell carcinoma, large cell carcinoma, and the like; specific examples of the adenocarcinoma include prostate carcinoma, small intestine carcinoma, endometrial carcinoma, cervical canal carcinoma, colorectal carcinoma, lung carcinoma, pancreatic cancer, esophageal carcinoma, rectal carcinoma, uterine carcinoma, gastric carcinoma, breast carcinoma, ovarian carcinoma, kidney cancer, hepatocarcinoma, gallbladder carcinoma, bile duct carcinoma, and the like; and specific examples of the squamous cell carcinoma include cervical canal carcinoma, eyelid carcinoma, conjunctival carcinoma, vaginal cancer, lung carcinoma, oral carcinoma, skin carcinoma, bladder carcinoma, tongue cancer, pharyngeal carcinoma, laryngeal carcinoma, esophageal carcinoma, and the like. Furthermore, examples of such tumors include sarcoma, leukemia, neuroma, melanoma, lymphoma, and a cancer of unknown primary and specific examples of the sarcoma include myogenic sarcoma.

Moreover, the "tumors" include cancer, sarcoma, and blood tumors.

Examples

The effectiveness of the method for selecting individuals to be a candidate for administration of an immune checkpoint inhibitor according to the present invention was confirmed by an examination of selection of individuals to be a candidate for administration of an anti-PD-1 antibody by B7-H3 immunohistological staining of tumor tissue from the following cases diagnosed as nonsmall-cell lung carcinoma.

The present invention is specifically described by the following Examples, but the present invention is not limited by the following Examples.
<Method of Examining>
(Cases to be Tested)

Cases histopathologically diagnosed as nonsmall-cell lung carcinoma were used (n=50).
(Type of Specimen)

Tumor tissue taken by a test with a bronchoscope for diagnosis purposes or tumor tissue taken by surgical operations were used. The tumor tissues were those obtained from primary lesions or tissues of metastatic lesions.

The tumor tissues used were those fixed with formalin and then stored as paraffin-embedded blocks.
(Staining of B7-H3 Protein)

Non-stained slice sections with a thickness of 4 microns were prepared from the aforementioned formalin fixed, paraffin-embedded blocks of tumor tissue and placed on a Platinum PRO micro slide glass (a product made by Matsunami Glass Ind., Ltd.) to prepare two microscope slides each.

One of the prepared microscope slides was stained with hematoxylin-eosin (HE) and used to confirm that tumor cells were present in the tissue.

One of the remaining microscope slides was used for immunohistochemistry (immunostaining) of the B7-H3 protein. In this staining, positive control slides and negative control slides with the primary antibody were stained at the same time. As positive controls, microscope slides on which cell blocks prepared from CHO-K1 cells in which human B7-H3 had been forcibly expressed (purchased from ATCC), and three kinds of cultured human tumor cells having different B7-H3 expression levels (MDA-MB-231 (purchased from ATCC), NCI-H322 (purchased from ECACC), and NCI-N87 (purchased from ATCC)) were used and the negative controls were: staining of slides on which cell blocks prepared from CHO-K1 cells in which only the vector had been introduced; and staining with a normal murine IgG antibody that does not recognize B7-H3 as a primary antibody.

The immunostaining was conducted with an automatic immunostaining apparatus (Ventana Benchmark XT, Roche Diagnostics) and the Ventana ultraView DAB universal kit (Roche Diagnostics) was used as the detection system.

Paraffin sections were deparaffined with the EZ prep buffer (Roche Diagnostics) at 75-76° C. for 8 minutes and then pretreated with the CC1 buffer (pH 8.5, Roche Diagnostics) solution at 95-100° C. for 60 minutes for antigen activation. Subsequently, the sections were reacted with an inhibitor reagent for 4 minutes, with the primary antibody (anti-B7-H3 antibody BD/5A11 (prepared in Daiichi Sankyo Co., Ltd.) or a normal murine IgG antibody) for 60 minutes, with an HRP-labelled secondary antibody for 8 minutes, and with a chromogenic substrate (DAB) for 8 minutes in this order (reagents that constitute the kit except primary antibodies).

The anti-B7-H3 antibody BD/5A11, which is the primary antibody used in this Example, is an antibody that is equivalent to commercially available antibodies (an anti-human B7-H3 antibody (AF1027, a product made by R & D SYSTEMS) and an anti-CD276 antibody (6A1, Abcam plc.)) and was prepared by the Applicant. These commercially available antibodies may be used instead of the anti-B7-H3 antibody BD/5A11 and similar results can be obtained with them.

These operations were conducted at 37° C. and washing was conducted between the operations. After the comparison staining with hematoxylin, the sections were dehydrated and penetrated with alcohol and xylene and enclosed.
(Method for Determining B7-H3 Staining)

The determination was made by pathology specialists authorized by Japanese Society of Pathology using the stained slides according to the following observation procedure.
1. Specific staining and the staining intensity were confirmed by using positive and negative control slides.
2. The position of tumor cells was confirmed using HE stained slides. In this confirmation, only tumor cells in the portion of infiltration were examined, but tumor cells outside of the portion of infiltration were excluded.
3. B7-H3 protein positive staining images of tumor cells in the specimen tissue, the intensity of positive staining, and the positive cell rate were observed using a 4× objective lens of an optical microscope. After switching the objective lens to 10×, whether positive staining was located on the cell membrane or in the cytoplasm was confirmed. Those in which the positive staining was observed only in the cytoplasm were considered as negative.
4. When the positive staining image on the cell membrane was not observed, further observation with a 20× objective lens was made.

In the determination of B7-H3 expression, only the staining and the staining intensity on the cell membrane of tumor cells were considered. The staining in the cytoplasm was excluded from consideration. The staining on the cell membrane was classified with the evaluation criteria for tissue immunological staining set forth in Table 1 below.

The following criteria conform to the HER2 IHC evaluation criteria in breast cancer (Guidelines for HER2 testing in breast cancer, the fourth edition) by Breast Cancer HER2 Testing Pathology Group based on the guidelines by American Society of Clinical Oncology (ASCO) (see Journal of Clinical Oncology, 2013, Vol. 31, No. 31, p. 3997-4013).

TABLE 1

| Consideration of (Expression level) | IHC score | Staining pattern |
|---|---|---|
| Positive | 3+ | [1] Tumor cells with strong and complete circular cell membrane staining > 10% |
| | 2+ | [2] Tumor cells with incomplete and/or weak to moderate and complete circular cell membrane staining > 10% or Tumor cells with strong and complete circular cell membrane staining ≤ 10% |
| | 1+ | [3] Tumor cells with partial cell membrane staining > 10% |
| Negative | 0 | [4] No staining or Tumor cells with incomplete and slight or faint cell membrane staining ≤ 10% |

The assessment of B7-H3 expression level as positive and negative was considered as described above, where the specimens for which it was impossible to make a consideration, due to the tumor tissue being crushed and the like, were excluded.

The results are shown in FIG. 2.

(Method for Clinical Evaluation (Antitumor Evaluation))

For the cases for which treatment with Nivolumab, an anti-PD-1 antibody therapeutic agent, was made, the evaluation of the relationship between the antitumor effect thereof and the B7-H3 expression level for each case was made, along with considering the B7-H3 expression level to be positive/negative.

The definition of the subjects of this analysis was as follows:
the patients who were treated by transvenous administration of 3 mg/kg per body weight of Nivolumab once in two weeks in the past,
the patients who had been treated with Nivolumab at least once,
the patients having a measurable lesion based on the criteria of RECIST ver1.1.

In the method of evaluating the antitumor effect, the evaluation was conducted based on the criteria of RECIST ver1.1

Specifically, "complete response (CR)" refers to the state in which all target lesions have disappeared and the short diameters of all lesions selected as target lesions have reduced to shorter than 10 mm and "partial response (PR)" refers to the state in which the sum of diameters of the target lesions has more than 30% decrease in comparison with the sum of diameters at the time of baseline evaluation. The cases considered as complete response or partial response were defined as the "cases of response".

In contrast, "progressive disease (PD)" refers to the state in which the sum of diameters of the target lesions has 20% or more increase in comparison with the smallest sum of diameters that exists at any time during the course (when the baseline diameter sum is the smallest that exists at any time during the course, then the baseline diameter sum is used as the smallest diameter sum) and also the sum of diameters has increased by 5 mm or more in absolute terms and "stable disease (SD)" refers to the state in which there is no reduction corresponding to PR and no increase corresponding to PD in comparison with the smallest sum of diameters that exists at any time during the course. The cases considered as progressive disease or stable disease were defined as "cases of non-response".

The results are shown in FIG. 3.

<Result 1. Evaluation of B7-H3 Expression Level in Tumor Tissue>

FIG. 2 illustrates examples of human tumor tissues for which the B7-H3 IHC score was rated as 3+, 2+, 1+, or 0 in B7-H3 immunohistological staining (IHC).

<Result 2. Relation Between Antitumor Effect of Preparation Containing Anti-PD-1 Antibody (Nivolumab) and B7-H3 Immunohistological Staining Result in Nonsmall-Cell Lung Carcinoma>

FIG. 3(A) illustrates the B7-H3 IHC score in cases of response to an anti-PD-1 antibody in nonsmall-cell lung carcinoma; FIG. 3(B) illustrates the B7-H3 IHC score in cases of non-response to the anti-PD-1 antibody in nonsmall-cell lung carcinoma; FIG. 3(C) illustrates the number of cases in which the B7-H3 expression level was positive (B7-H3 (+), the cases in which the B7-H3IHC score was 3+, 2+, or 1+), the number of cases in which the B7-H3 expression level was negative (B7-H3 (−), the cases in which the B7-H3IHC score was 0), and the response rate in (A) and (B).

As shown in FIG. 3(C), the cases considered as responsive in the cases for which the expression level of B7-H3 was positive (B7-H3 (+)) were as low as 29%, while the cases considered as responsive were as high as 88% in the cases for which the expression level of B7-H3 was negative (B7-H3 (−)) (Fischer's exact test: p=0. 0031, significantly different).

From this result, it can be determined that the preparation containing an anti-PD-1 antibody (Nivolumab) is not effective for the nonsmall-cell lung carcinoma in which the expression level of B7-H3 was positive.

Accordingly, unnecessary treatment can be avoided by removing patients having a tumor tissue for which the B7-H3 expression level is considered to be positive from patients to be a candidate for administration of an immune checkpoint inhibitor.

Meanwhile, efficient treatment is possible by determining that patients having a tumor tissue for which the B7-H3 expression level is considered to be negative are candidates for treatment with an immune checkpoint inhibitor.

The foregoing results suggest that the B7-H3 protein may be a clinically important biomarker in treatment with a preparation containing an anti-PD-1 antibody.

INDUSTRIAL AVAILABILITY

Use of a method for selecting individuals to be a candidate for administration of an immune checkpoint inhibitor according to the present invention makes it possible to select individuals for whom an immune checkpoint inhibitor will be effective more accurately.

Since the present invention makes it possible to determine the probability that an immune checkpoint inhibitor is effective before treatment, it is possible to avoid ineffective treatment that requires a large amount of medical expense, but is not expected to be effective, despite the existence of cases in which the immune checkpoint inhibitor is hardly likely to be effective.

The invention claimed is:
1. A method for increasing efficiency of an immune checkpoint inhibitor treatment, the method comprising:
(1) a step of collecting a tumor tissue from the individual,
(2) a step of determining the extent of B7-H3 expression in the tumor tissue collected in step (1),

(3) a step of selecting the individual as an individual to be a candidate for administration of an immune checkpoint inhibitor if the B7-H3 expression level is considered to be negative, and (4) administering the immune checkpoint inhibitor to the individual with the B7-H3 expression level that is considered to be negative, wherein the immune checkpoint inhibitor is an anti-PD-1 antibody, and/or an anti-PD-L1 antibody.

2. The method for increasing the efficiency of the immune checkpoint inhibitor treatment according to claim 1, wherein step (2) comprises a step of conducting immunohistological staining of B7-H3.

3. The method for increasing the efficiency of the immune checkpoint inhibitor treatment according to claim 1 or 2, wherein the tumor is nonsmall-cell lung carcinoma, small cell lung carcinoma, neuroendocrine tumor, squamous cell carcinoma, adenocarcinoma, sarcoma, leukemia, neuroma, melanoma, lymphoma, or a cancer of unknown primary.

4. The method for increasing the efficiency of the immune checkpoint inhibitor treatment according to claim 3, wherein the nonsmall-cell lung carcinoma is adenocarcinoma, squamous cell carcinoma, or large cell carcinoma.

5. The method for increasing the efficiency of the immune checkpoint inhibitor treatment according to claim 3, wherein the adenocarcinoma is prostate carcinoma, small intestine carcinoma, endometrial carcinoma, cervical canal carcinoma, colorectal carcinoma, lung carcinoma, pancreatic cancer, esophageal carcinoma, rectal carcinoma, uterine carcinoma, gastric carcinoma, breast carcinoma, ovarian carcinoma, kidney cancer, hepatocarcinoma, gallbladder carcinoma, or bile duct carcinoma.

6. The method for increasing the efficiency of the immune checkpoint inhibitor treatment according to claim 3, wherein the squamous cell carcinoma is cervical canal carcinoma, eyelid carcinoma, conjunctival carcinoma, vaginal cancer, lung carcinoma, oral carcinoma, skin carcinoma, bladder carcinoma, tongue cancer, pharyngeal cancer, laryngeal carcinoma, or esophageal carcinoma.

7. The method for selection according to claim 3, wherein the sarcoma is myogenic sarcoma.

8. A method for treating a tumor, comprising treating an individual by increasing the efficiency of the immune checkpoint inhibitor treatment according to claim 1, wherein the immune checkpoint inhibitor contacts the tumor.

9. The method for treating a tumor according to claim 8, wherein the immune checkpoint inhibitor is an immune checkpoint inhibitor comprising an anti-PD-1 antibody, and/or an anti-PD-L1 antibody.

\* \* \* \* \*

UNITED STATES PATENT AND TRADEMARK OFFICE
CERTIFICATE OF CORRECTION

PATENT NO. : 11,371,995 B2
APPLICATION NO. : 16/473615
DATED : June 28, 2022
INVENTOR(S) : Yonesaka et al.

It is certified that error appears in the above-identified patent and that said Letters Patent is hereby corrected as shown below:

In the Claims

| Column | Line | |
|---|---|---|
| 11 | 15 | change "claim" to -- claims -- |

Signed and Sealed this
Twenty-eighth Day of March, 2023

Katherine Kelly Vidal
*Director of the United States Patent and Trademark Office*